United States Patent [19]

Moy

[11] Patent Number: 5,540,231
[45] Date of Patent: Jul. 30, 1996

[54] METHOD AND APPARATUS FOR MEASURING BLOOD PRESSURE

[76] Inventor: Bradford K. Moy, 519 Oak Park Dr., San Francisco, Calif. 94131

[21] Appl. No.: 411,081

[22] Filed: Mar. 27, 1995

Related U.S. Application Data

[63] Continuation-in-part of Ser. No. 95,649, Jul. 21, 1993, abandoned.

[51] Int. Cl.$^6$ ................................................ A61B 5/00
[52] U.S. Cl. ............................................ 128/677; 128/680
[58] Field of Search ........................... 128/672, 677–683, 128/686, 687; 606/202

[56] References Cited

U.S. PATENT DOCUMENTS

| | | | |
|---|---|---|---|
| 1,089,122 | 3/1914 | Faught et al. | 128/677 |
| 4,088,126 | 5/1978 | Gemind | 18/677 |
| 4,492,234 | 1/1985 | Arkans | 128/677 |
| 4,938,226 | 7/1990 | Danielsson et al. | 128/679 |

*Primary Examiner*—Angela D. Sykes
*Assistant Examiner*—Robert L. Nasser, Jr.

[57] ABSTRACT

An improved apparatus and method for measuring blood pressure. The user operates a manual, foot-powered air pump having a set switch to supply air of varying volumes per stroke to a sphygmomanometer, reducing strain to the hands, wrists and forearm.

4 Claims, 4 Drawing Sheets

METHOD AND APPARATUS FOR MEASURING BLOOD PRESSURE

This patent application is a Continuation-in-part of patent application Ser. No. 8/095,649, Entitled Method And Apparatus For Measuring Blood Pressure, filed Jul. 21, 1993, now abandoned.

BACKGROUND OF THE INVENTION

1. Field of the Invention

This invention relates to: blood pressure measuring devices and particularly concerns an improved method and apparatus for measuring blood pressure, specifically by modifying a conventional sphygmomanometer to allow the user to more easily and inexpensively conduct the measurement of systolic and diastolic blood pressures.

2. Background and Related Disclosures

The conventional method and apparatus most commonly used for measuring blood pressure in a physician's office involves the use of a sphygmomanometer, which includes an inflatable cuff, a pressure gauge, a bleed valve, a check valve and a hand-held resilient inflation bulb pump to supply air pressure to inflate the cuff, all cooperating in pneumatic communication with one another.

The user wraps and secures the inflatable cuff around the upper arm (or leg) of the patient and inflates the cuff by squeezing the hand-held inflation bulb one or more times until, in the case of an arm, the brachial aderial blood flow is arrested by the inflating cuff. Inflation cuffs come in various sizes, a larger cuff, known as an obese or thigh cuff, is used on individuals with larger arms or on the thigh, respectively.

The cessation of arterial blood flow is usually monitored by using a stethoscope or electronic indicator, held with the other hand and placed over the brachial artery as it passes through the antecubital fossa of the arm. The bleed valve is opened to release pressure while the user listens for the recurrence of aderial blow flow, the auscultatory "Korotkov sound," where a wave of blood is released, which indicates that the patient's own blood pressure has overcome the pressure exerted by the inflatable cuff: this indicates the systolic blood pressure. The user continues to deflate the cuff until the arterial pressure no longer must overcome the pressure of the inflatable cuff, listening for disappearance of the Korotkov sound, which indicates that the blood pressure is no longer working against the air pressure in the inflatable cuff: this indicates diastolic blood pressure.

Blood pressure is usually measured in millimeters of mercury (mmHg.) and expressed as systotic/diastolic. Blood pressure has a normal range of about 100–130 mmHg. for systolic and 60–80 mmHg. for diastolic, with a wide variation depending on the blood pressure of the patient.

The above method is adequate and apparatus have been used for years. However, repetitively squeezing the inflation bulb to inflate the cuff can cause muscle strain and repetitive motion injuries (such as carpal tunnel syndrome in the wrist and/or lateral epicondylitis in the elbow) when the user is taking a large number of blood pressure measurements, or a small number of measurements each day over time. In addition, it is sometimes necessary to use the larger inflatable obese cuff on obese patients, requiring many more squeezes of the hand-held inflation bulb, exacerbating the above-described problem of muscle strain.

The above method and apparatus also requires that the user rather awkwardly hold and manipulate instruments in either hand, the bulb/bleed valve in one and the stethoscope in the other.

Attempts in the past to overcome the problem have required expensive and cumbersome electrical equipment and motors, which further require a source of electricity and likely returns a less accurate measurement than the conventional method. Air pumps powered by an electrical motor have been used in the past to inflate the cuff but a certain, sometimes critical, amount of accuracy is sacrificed for the convenience of this apparatus. Typically the user has insufficient control over the inflation and/or deflation rates of the cuff when using an electric air pump, being limited to turning the electric pump on or off. Should the patient have a slow pulse rate, the cuff pressure can climb or fall significantly between pulses. Systolic and diastolic blood pressures are measured by the occurrence and cessation of the pulse and, should the air pressure of the cuff climb or fall rapidly between two pulses, the resulting readings will reflect incorrect pressures.

Manually powered pumps: such as inflation bulbs, allow the user to control the flow of air much more closely because the user must himself supply the physical work for every millibar of pressure and so can regulate the amount and rate of air delivery with great accuracy.

Two factors must be balanced when determining a good air pump volume to be used with a given inflatable cuff. If too many squeezes are required to inflate the cuff then the user will become fatigued and vulnerable to the repetitive motion injuries discussed above. If too few squeezes are required to inflate the cuff then the user is delivering a relatively large volume of air witch each squeeze or stroke and hence fine control of the volume of air delivered is diminished.

SUMMARY OF THE INVENTION

The present invention provides a simple and inexpensive system for measuring blood pressure and overcoming the above problems.

Foot-powered air pump means, comprising a typical foot-powered air pump, is attached to the sphygmomanometer, quickly and easily inflating the cuff to impede the flow of arterial blood without hand strain or the need for other equipment. A single depression of the foot-powered air pump means by a user's foot is termed a stroke.

The foot-powered pump means incorporate a set switch means designed to enable the user to set the pump means to deliver different volumes of air to the cuff per stroke of the pump means. A set switch setting causing a given amount of air to be evolved per stroke is selected to match a given size inflation cuff. With a larger inflation cuff the user sets the pump to deliver a greater amount of air per stroke.

The foot-powered air pump employed can be of any type commonly available and well known in the art, such as a bellows or piston type of pump, A typical foot-powered pump is modified by including a set switch. This set switch has two or more settings, allowing the foot-powered pump to deliver a different volume of air per stroke to the pump depending on the setting used.

The foot-powered air pump can be attached by means of a conduit in pneumatic communication at any point on the sphygmomanometer, to the cuff, the hand-held inflation bulb or to the conduit which connects the various elements of the sphygmomanometer.

It is therefore an object of this invention to provide a simple, inexpensive and ergonomic device and method to measure blood pressure. Other objects and advantages of this invention will be both apparent and detailed hereinafter set forth. The invention accordingly consists in the method, elements and arrangement of parts set forth below and will be indicated in the claims set forth below.

DETAILED DESCRIPTION OF THE DRAWINGS

Figure 1:
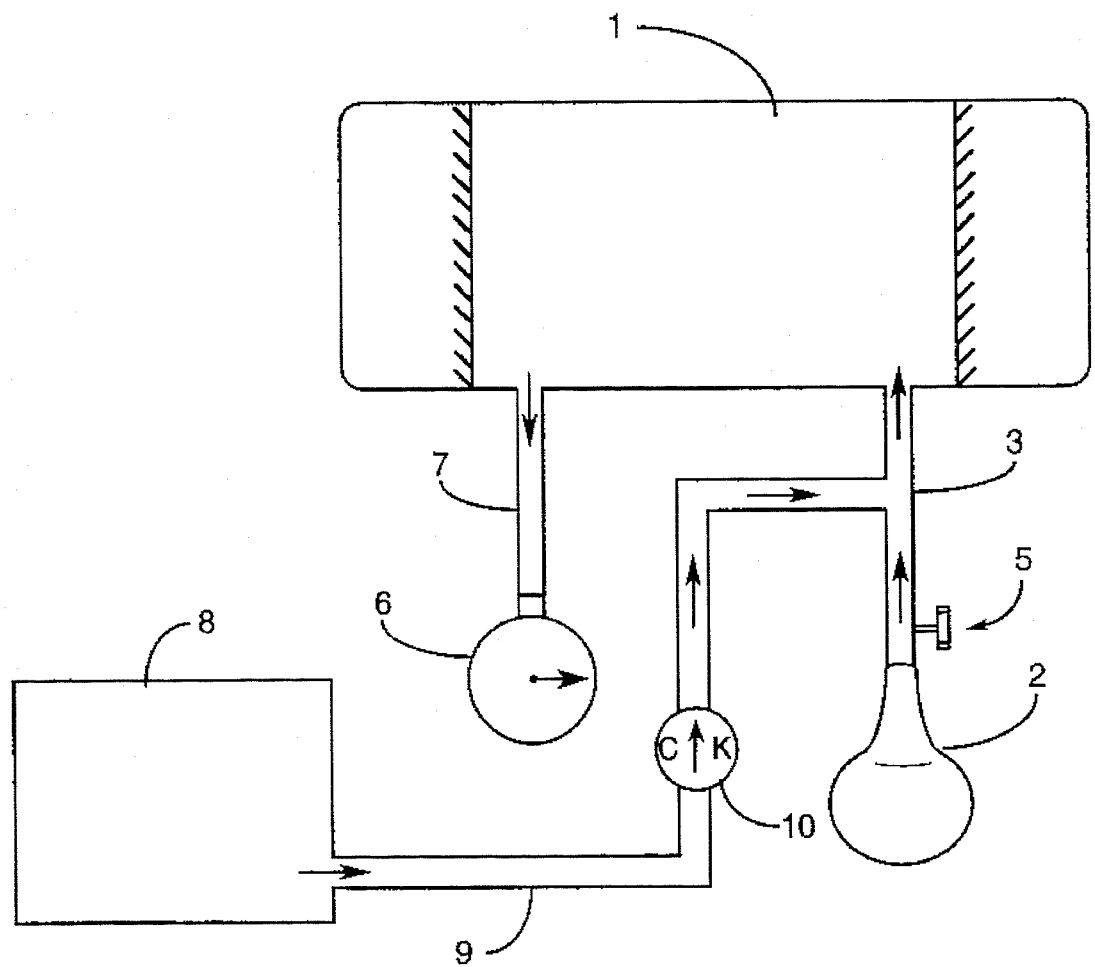
FIG. 1 is a schematic view of one embodiment of the system of the present invention.

Referring now to FIG. 1 the invention is depicted with the preferred embodiment including an inflatable cuff 1 of the kind well known in the art, pneumatically connected to inflation bulb 2 by conduit 3. Pressure can be created by inflation bulb 2 by repeatedly squeezing the bulb, there is also a bleed valve 5 to release the pressure. The inflatable cuff 1 is further pneumatically connected to pressure gauge 6 by conduit 7. In this embodiment the foot-powered air pump means 8 is pneumatically connected to conduit 3 by conduit 9, which has a one-way check valve 10 connected in-line, so pressure can also be created by repeatedly depressing foot-powered air pump 8. Arrows depict the direction of air pressure during inflation.

The inventor considers this to be the best mode of this invention because a kit can be easily supplied to modify an existing sphygmomanometer wherein the user is supplied with foot-powered air pump 8, conduit 9, with one-way check valve 10, which is then connected to conduit 3 by the user by means of a common T-fitting. This drawing is simply one embodiment of the system and it would be readily apparent to one of ordinary skill in the art that conduit 10 can be alternatively connected to the sphygmomanometer at any point where it could be sealably connected in pneumatic communication with the inflation cuff to produce the same result.

Figure 2B:
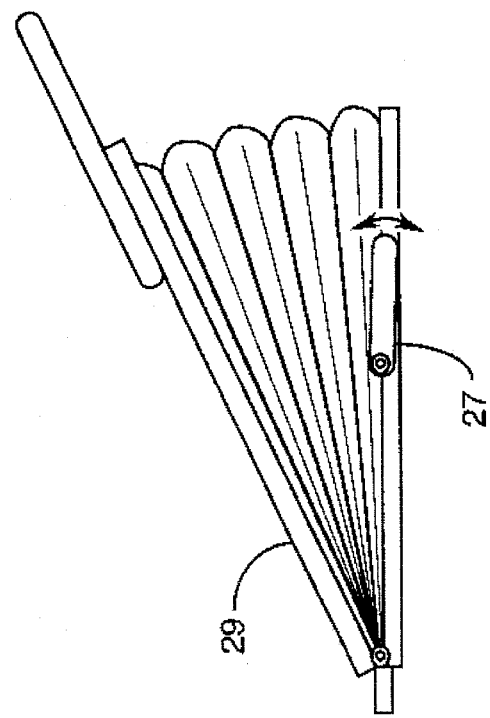
FIGS. 2a is a detail side cut-away view and 2b is a side detail view of embodiments of the foot-powered air pump means of the present invention.
Figure 2A:
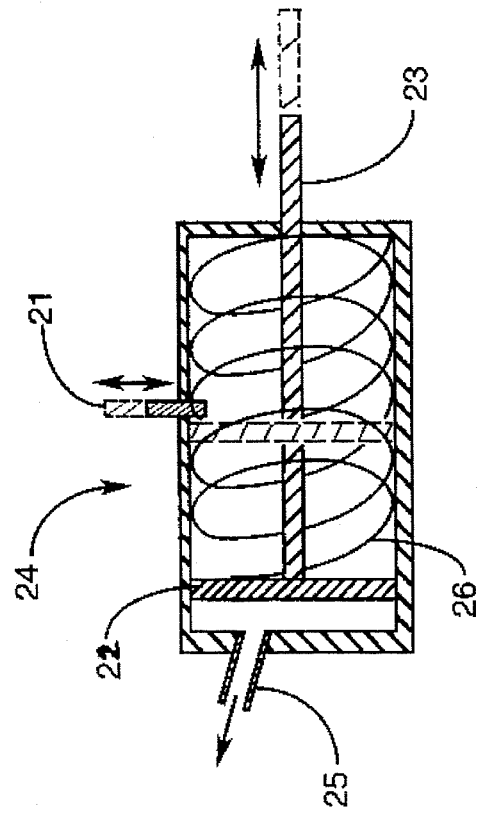

Referring now to FIGS. 2a and 2b, typical foot-powered air pumps modified with a set switch are depicted.

FIG. 2a shows the cylinder of a typical air pump of the piston type with a set switch 21. These foot-powered air pumps are well known in the art and utilize a piston 22 having a connecting rod 23 fixedly attached normal to the piston. The user depresses a pedal mechanically linked to the connecting rod (not shown)that forces the piston to run the length of a cylinder 24 to force air out an exhaust port 25 at the distal end. The piston is returned to its starting position by means of a coil spring 26 and the process is repeated as often as is necessary to deliver a sufficient amount of air pressure. In this case a sufficient amount of air pressure is that amount sufficient to inflate a given inflatable cuff (not shown) after a few strokes.

The set switch 21 is a stop that prevents the piston from returning to its initial starting position. The stop fits through the wall of the cylinder in this case and when it is inserted into the cylinder it causes the travel of the piston to be decreased and the volume of air delivered per to be decreased proportionately.

FIG. 2b depicts a set switch stop 27 being used on a bellows type of foot-powered air pump. The stop may be hindgeably attached to the floor of the bellows 29 and, when raised, causes the bellows to be depressed less with each stroke, resulting in a smaller delivery of air pressure with each stroke.

Figure 3B:
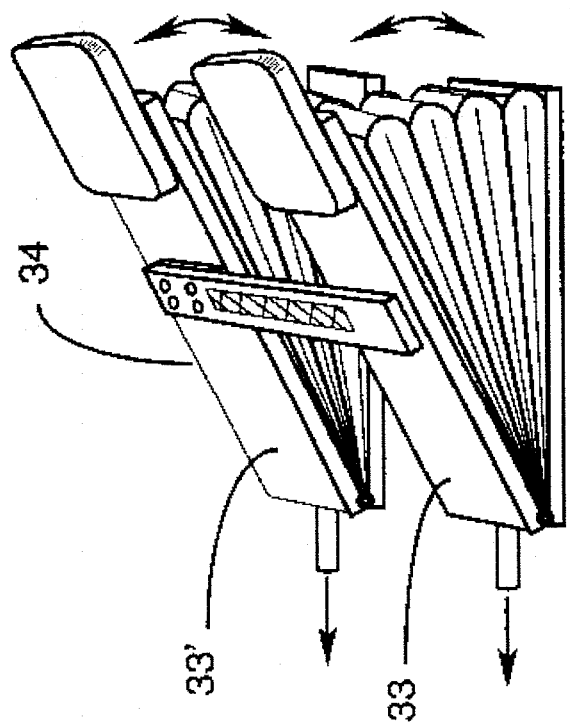
FIGS. 3a and 3b are perspective views of alternative embodiments of the foot-powered air pump means of the present invention.
Figure 3A:
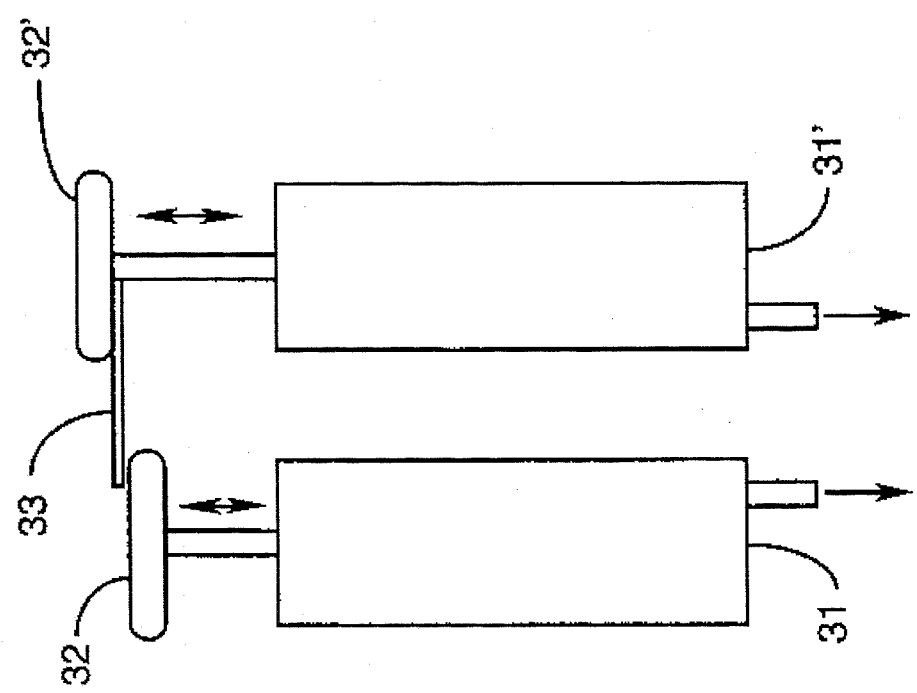

FIGS. 3a and 3b depict another approach to using a set switch for variable delivery of air.

FIG. 3a depicts the connecting rods of two cylinders 31 and 31' connected to two pedals 32 and 32'. A crossbar 33 is used so that when pedal 32 is depressed only one piston is actuated. When pedal 32' is depressed however, both pistons are actuated, delivering the sum of the volumes of air produced by the two pistons.

Similarly, FIG. 3b depicts the bellows of two foot-powered bellows type air pumps, 33 and 33' being connected by crossbar 34. When bellows 33 is depressed only one bellows is actuated. When bellows 33' prime is depressed however, both bellows are actuated, delivering the sum of the volumes of air produced by the two bellows.

It will be apparent to one of ordinary skill in the art that there are a number of ways to modify the foot-powered pump means to allow it to deliver variable quantities of air per stroke. It will also be apparent to one of ordinary skill in the art that the foot-powered pump means can have more than two or more set switches incorporated into it to allow the selection of more than two different volumes of air to be forced per stroke. For instance, in the embodiments of FIGS. 3a and 3b, three or more pumps could be used in parallel with the appropriate arrangement of crossbars.

The bleed valve used in the above embodiments is a needle valve with the tip of the screw blocking a hole in the pressurized system. This is simply an illustrative embodiment of any number of bleed valves and any sort of equivalent bleed valve, which are well known in the art, could be used instead.

The one-way check valve is connected in-line between the foot-powered air pump and the inflatable cuff and operates to allow air to pass through it in one direction but not the other. This prevents air from escaping back through the foot-powered air pump after it has been sent to the inflatable cuff. There are many one-way check valves, well known in the art which can be used.

The pressure gauge can be of any type, electrical or mechanical. The most common type of pressure gauge used is a mechanical analog dial displaying pressure in millimeters of mercury.

OPERATION OF THE SPHYGMOMANOMETER

Figure 4:
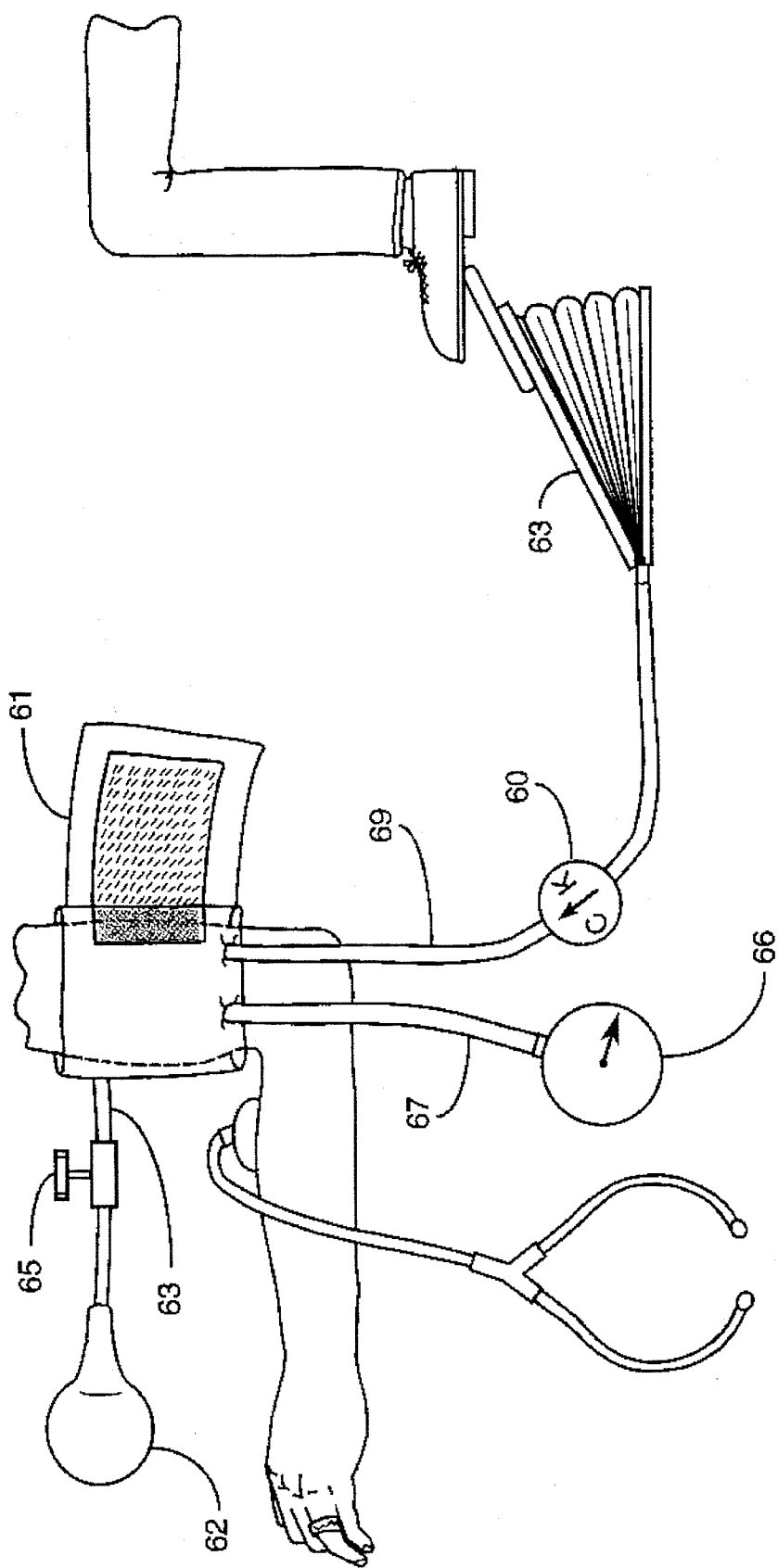
FIG. 4 and is a schematic view illustrating the operation of the present invention.

Referring now to FIG. 4 the operation of the invention is depicted with the same configuration as seen in FIG. 1. Inflatable cuff 61 is wrapped around the patient's arm. The cuff is pneumatically connected directly to foot-powered air pump 68 (incorporating set switch 68') by conduit 69, which has the one-way check valve 60 connected in-line. The inflatable cuff 41 is further pneumatically connected to pressure gauge 66 by conduit 67 and also connected to inflation bulb 62 by conduit 63, which has a bleed valve 65.

The user first adjusts the air pump set switch 68' to deliver a convenient amount of air per stroke to inflation cuff 61. What is a convenient amount of air is of course a subjective decision of the user, but it is suggested that most users would find about five strokes to inflate a given cuff to maximum pressure to be a convenient amount of air per stroke. Hence, the larger obese cuff would require a setting which allows a larger volume of air to be sent per stroke.

The user wraps and secures the inflatable cuff around the upper arm of the patient and inflates the cuff by repetitively stepping on the foot-powered air pump until brachial arterial blood flow is arrested. The cessation of arterial blood flow is typically monitored when taking blood pressure from an arm by using a stethoscope or microphone or electronic indicator placed over the brachial artery as it passes through the antecubital fossa, although the user can place the stethoscope or indicator over any appropriate artery.

The bleed valve 65 is then opened to slowly release pressure while the user listens for the recurrence of arterial blow flow, a Korotkov sound where a wave of blood is released into the artery by the heart's pumping action, which indicates that the patient's own blood pressure has overcome the pressure exerted by the inflatable cuff, thus indicating systolic blood pressure. The user continues to deflate the cuff until the arterial pressure no longer must overcome the pressure of the inflatable cuff, listening for the disappearance of the Korotkov sounds which indicates that an equilibrium of pressures has been achieved, thus indicating diastolic blood pressure. The user then records these figures.

What is claimed is:

1. An apparatus for measuring blood pressure, comprising:
   (A) an inflatable cuff for stopping blood flow in a person's limb;
   (B) a pressure gauge, in pneumatic communication with said inflatable cuff, for indicating the pressure within said inflatable cuff;
   (C) bleed valve means for controllably releasing air pressure from said inflatable cuff;
   (D) foot-powered air pump means, said means using only mechanical energy provided by the user's leg to pump air, in pneumatic communication with said inflatable cuff, for supplying pressure to said inflatable cuff and further having one-way check valve means whereby air supplied by said foot-powered air pump means is prevented from flowing back through said pump, and
   (E) set switch means for setting said foot-powered air pump means to deliver a predetermined volume of air per stroke that a user applies to said foot-powered air pump means.

2. The apparatus of claim 1 wherein the foot-powered pump means incorporates a piston within a cylinder to pump air to said inflatable cuff.

3. The apparatus of claim 1 wherein the foot-powered pump means incorporates a bellows to pump air to said inflatable cuff.

4. A method for measuring blood pressure, comprising the steps of:
   (A) securing an inflatable cuff around an upper limb of a person;
   (B) determining a convenient amount of air per stroke of foot-powered air pump means to inflate said inflatable cuff;
   (C) setting set switch means on foot-powered air pump means to deliver the desired air per stroke of foot-powered air pump means;
   (D) operating foot-powered air pump means solely by providing mechanical energy to compress air with a user's leg to supply a pressure to said inflatable cuff until the pressure in said inflatable cuff exceeds the systolic blood pressure of a person;
   (E) releasing the pressure from said inflatable cuff while listening for Korotkov sounds, and
   (F) recording the systolic and diastolic blood pressure indicated by the Korotkov sounds.

* * * * *